(12) United States Patent
Reyman

(10) Patent No.: US 11,672,918 B2
(45) Date of Patent: Jun. 13, 2023

(54) SYRINGE WITH SELECTABLE METERING

(71) Applicant: Mark Reyman, Armonk, NY (US)

(72) Inventor: Mark Reyman, Armonk, NY (US)

( * ) Notice: Subject to any disclaimer, the term of this patent is extended or adjusted under 35 U.S.C. 154(b) by 427 days.

(21) Appl. No.: 17/061,555

(22) Filed: Oct. 1, 2020

(65) Prior Publication Data
US 2021/0106765 A1    Apr. 15, 2021

Related U.S. Application Data

(60) Provisional application No. 62/909,512, filed on Oct. 2, 2019.

(51) Int. Cl.
*A61M 5/315* (2006.01)
*A61M 5/46* (2006.01)

(52) U.S. Cl.
CPC .... *A61M 5/31576* (2013.01); *A61M 5/31511* (2013.01); *A61M 5/31525* (2013.01); *A61M 5/46* (2013.01); *A61M 2205/583* (2013.01)

(58) Field of Classification Search
CPC .......... A61M 5/31576; A61M 5/31511; A61M 5/31525; A61M 5/31505
See application file for complete search history.

(56) References Cited

U.S. PATENT DOCUMENTS

| | | | |
|---|---|---|---|
| 6,579,269 B1* | 6/2003 | Kleyman | A61M 5/31555 604/207 |
| 2015/0045740 A1* | 2/2015 | Kojima | A61M 5/31505 604/220 |

* cited by examiner

*Primary Examiner* — Bradley J Osinski
(74) *Attorney, Agent, or Firm* — Sofer & Haroun, LLP

(57) ABSTRACT

A needle syringe has a plunger and a needle for filling and dispensing liquid from the cavity. The cavity has finger clip with movable locking pins. The plunger has at least one set of grooves corresponding to a specific dosage for the needle syringe, the specific dosage of the groove being demarked by a marking ledge that indicates a change to a deeper depth section of the groove. The locking pins are configured to rest in the at least one set of grooves, such that when the plunger is removed, the locking pins pass within a first shallow section of the groove, pass over the ledge, and continue to pass in the deeper depth section of the groove. When the plunger is depressed in a first partial dispensing movement, the locking pins pass in the deeper depth section of the groove until the plunger depression is temporarily locked when the locking pins reach the ledge, where the dose remaining in the cavity is the specific dosage.

8 Claims, 4 Drawing Sheets

SYRINGE WITH SELECTABLE METERING

RELATED APPLICATION

This application claims the benefit of priority from U.S. Provisional Patent Application No. 62/909,512, filed on Oct. 2, 2019, the entirety of which is incorporated by reference.

FIELD OF INVENTION

This invention relates to syringes. More specifically, the present invention relates to a syringe in which the user is able to manually adjust and control a fixed dosage.

DESCRIPTION OF RELATED ART

Syringes have been used for over 100 years to provide precise doses of medication and other liquids. The typical syringe has a cavity, a moveable plunger, and an opening or needle. The plunger is set completely filling the cavity, the needle or opening is inserted into the desired liquid to be dispensed and the plunger is removed to a desired height in the cavity, pulling the liquid into the cavity. To dispense, the plunger is depressed, pushing out the liquid.

To set the amount of liquid to be dispensed the cavity is usually metered so that, for example, if you want to collect and dispense 0.5 ml, then with the opening disposed in the liquid, the plunger is pulled up until the bottom of the plunger would match a marking on the cavity of 0.5 ml, and then later the plunger would be depressed to eject that amount of liquid.

One common problem with that is that it requires a precise alignment of the plunger with the markings on the cavity to ensure an appropriate dosage. This is difficult for people with poor vision. Moreover, it is common in modern medicine that at home injections are used to dispense medicine and this is used frequently by elderly patients who have less dexterity in their fingers for measuring precise doses.

In the prior art, there are attempts to correct these issues, the first of which is simply providing separate syringes for separate doses, so instead of being metered, the cavity is set that when full it matches the desired dose. To use the plunger is pulled out entirely to a stop to fill the cavity and then depressed to dispense a liquid in the full amount of the cavity. However, this solution is inflexible and does not allow for modified dosages so someone would need to have multiple syringes on hand.

Other prior art designs have adjustable preset dosing settings where a user can limit a dosage to some portion of the cavity using a series of stops and barriers to limit plunger movement. Although such designs are for the same purpose they are complicated in design and require detailed manufacturing or otherwise are not ideally suited to their function.

OBJECTS AND SUMMARY

The present invention overcomes the drawbacks associated with the prior art and provides a syringe with selectable metering that is not only easy to use but also is simply constructed and inexpensive to manufacture.

A needle version of the syringe allows one to purposely overfill the syringe so that the inevitable introduction of some air in the barrel can then be evacuated along with the excess liquid when the plunger is then depressed until it finally stops at the predetermined, preset dosage. At that point, it is now ready to dispense the exact, proper dosage.

To this end a needle syringe is provided having a cavity, a plunger and a needle for filling and dispensing liquid from the cavity. The cavity has finger clip with movable locking pins. The plunger has at least one set of grooves corresponding to a specific dosage for the needle syringe, the specific dosage of the groove being demarked by a marking ledge that indicates a change to a deeper depth section of the groove.

The locking pins are configured to rest in the at least one set of grooves, such that when the plunger is removed, the locking pins pass within a first shallow section of the groove, pass over the ledge, and continue to pass in the deeper depth section of the groove. When the plunger is depressed in a first partial dispensing movement, the locking pins pass in the deeper depth section of the groove until the plunger depression is temporarily locked when the locking pins reach the ledge, where the dose remaining in the cavity is the specific dosage.

When the plunger is depressed in a second full dispensing movement, to dispense the specific dosage, the finger clip is configured to be pulled, deforming a bottom of the finger clip and moving the locking pins over the ledge, allowing the locking pins to re-enter shallow section of the groove and dispensing the specific dosage from the needle syringe.

In another embodiment, an oral syringe is provided having a cavity, a plunger, and a nozzle for filling and dispensing liquid from the cavity. The cavity has finger clip, the finger clip having movable locking pins. The plunger has at least one set of grooves corresponding to a specific dosage for the oral syringe, the specific dosage of the groove being demarked by a stop whole in the groove.

The locking pins are configured to rest in the at least one set of grooves, such that when the plunger is removed, the locking pins pass within the groove and into the locking hole, filling the cavity with the specific dosage. When the plunger is depressed, to dispense the specific dosage, the finger clip is configured to be pulled, deforming a bottom of the finger clip and moving the locking pins out of the locking holes, allowing the locking pins to re-enter the groove and dispensing the specific dosage from the oral syringe.

BRIEF DESCRIPTION OF THE DRAWINGS

The present invention can be best understood through the following description and accompanying drawing, wherein.

DETAILED DESCRIPTION

Figure 1A:
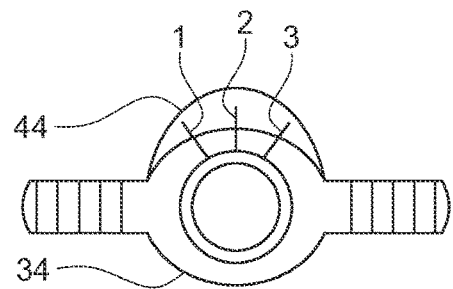
FIG. 1A illustrates a needle syringe cavity from the top with finger clip and indicator markings in accordance with one embodiment.
Figure 1B:
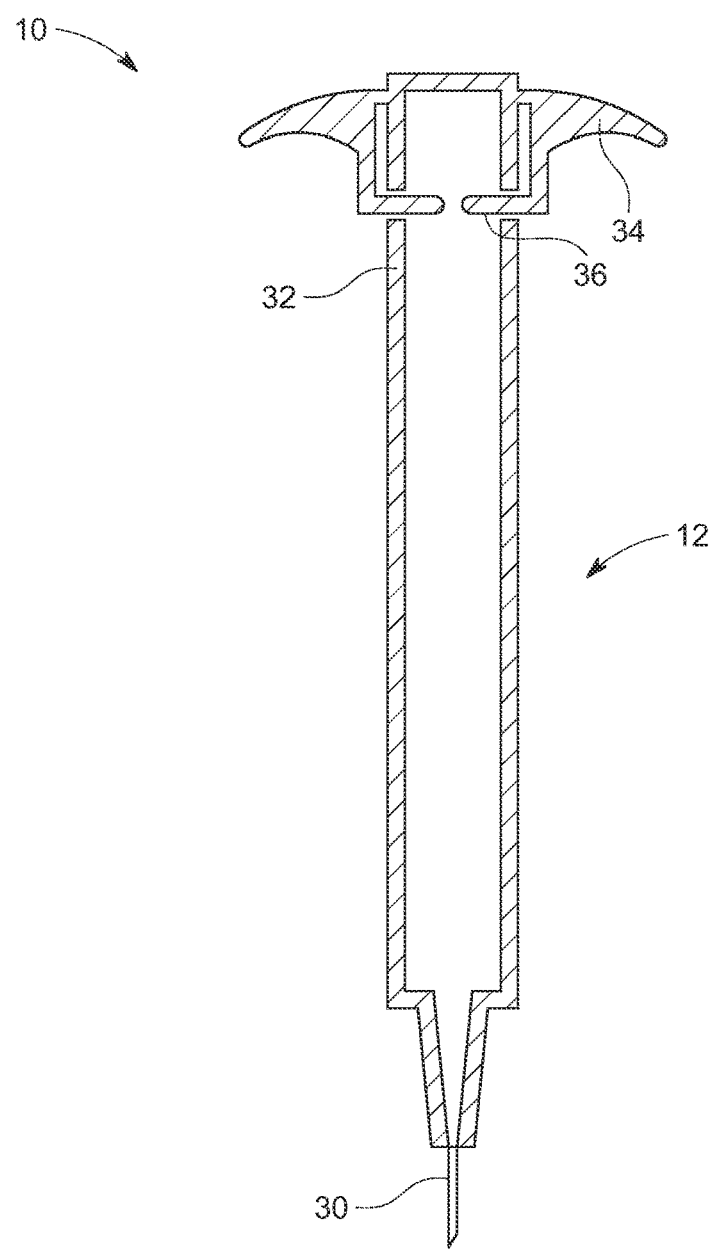
FIG. 1B, illustrates a side view of the cavity in accordance with one embodiment.
Figure 1C:
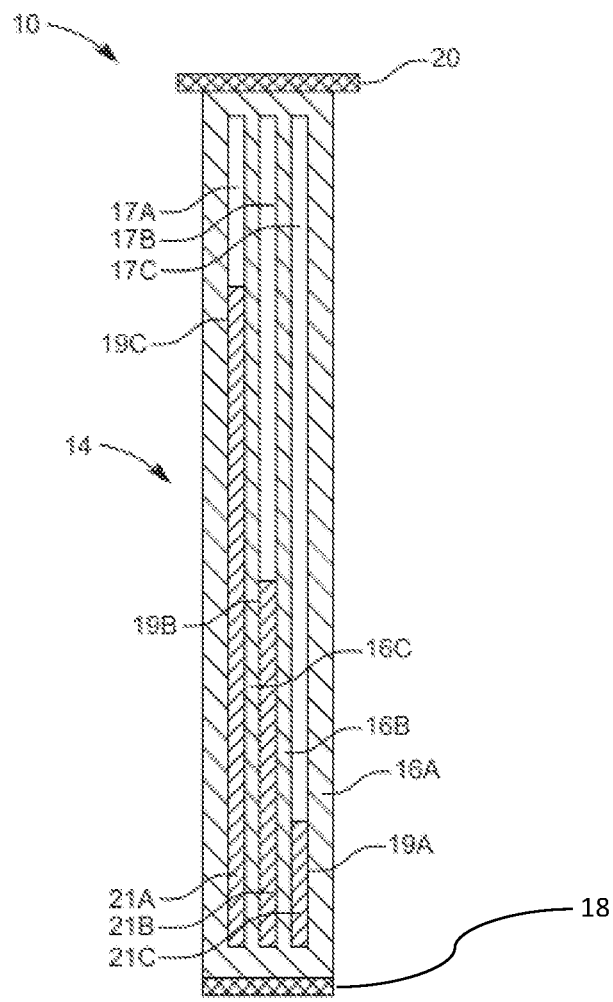
FIG. 1C, illustrates a side view of a plunger for the cavity of the needle syringe in accordance with one embodiment.
Figure 1D:
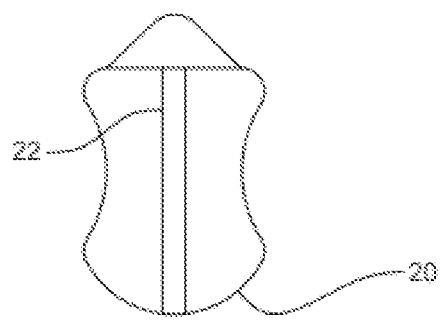
FIG. 1D, illustrates a top view of the plunger with an indicating arrow in accordance with one embodiment.

In one embodiment as shown in FIGS. 1A-1D, a needle syringe 10 is shown having a cavity 12 and plunger 14. As shown in FIG. 1C, plunger 12 has three grooves 16A-16C, each representing a different dosage, described in more detail below. It is understood that plunger 14 could have additional or fewer grooves 16, such as a single groove for a single dosage, but for the present example three (3) grooves 16A-16C is used to illustrate the salient features of the invention. At the bottom of plunger 14 is a gasket 18 to slidingly seal against the walls of cavity 12 as in a normal syringe. At the top of plunger 14 is a pressing surface 20. As shown in FIG. 1D, pressing surface 20 has an indicator arrow 22 that is used to correctly orient plunger 14 within cavity 12 in a manner to dispense the correct dose as explained in more detail below.

As shown in FIG. 1B, cavity 12 has a needle 30, and pin openings 32 as well as a connected finger grip 34 and locking pins 36. Finger grip 34 is fixedly connected to the top of cavity 12. As illustrated in FIG. 1B locking pins 36 extend below the body of grip 34, down the side of cavity 12 into pin openings 32.

As shown in FIG. 1C, plunger 14 has three sets of grooved 16A-16C, each extending a different length along the long axis of plunger 14. In this embodiment for needle syringe 10, grooves 16A-16C each have a segment 17A-17C corresponding to a dose amount, ledges 19A-19C and cutouts or deep grooves 21A-21C.

At the outset, when plunger 14 is disposed entirely within cavity 12, pins 36, passing through pin opening 32, are configured to rest in one of grooves/indentations 16A-16C (not shown but indentations 16A-16C are each a pair of indentations on opposite sides of plunger 14, one for each pin 36). More specifically, at the outset, pins 36 rest in one of segments 17A-17C.

Regarding the dosage selection, as shown in FIG. 1A, the top of finger grip 34 has three indicator markings 44, each of which designate a corresponding one of grooves 16A-16C. By matching indicator arrow 22 of pressing surface 20 of plunger 14 within cavity 12 to one of markings 44, it orients plunger 14 so that pins 36 are in the desired groove 16. Again, as noted above, the example shown has three (3) grooves 16A-16C but in another embodiment, plunger 14 can be equally constructed with a single set of grooves 16, such as solely groove 16A, but the examples of the functions of syringe 10 are set forth in this specification using the example of a multi-dose syringe 10 with three grooves 16A-16C.

For example, exemplary needle syringe 10 may be configured to dispense either 0.25 mL, 0.5 mL, or 0.75 mL. As such plunger 14 has three grooves 16A, 16B, and 16C each relating to either 0.25 mL, 0.5 mL, or 0.75 mL respectively. Indicator markings 44 on finger grip 34 likewise would indicate 0.25 mL, 0.5 mL, or 0.75 mL. So, when a user wants to implement syringe 10 for 0.5 mL, the user would rotate plunger 14 until indicator arrow 22 on the top points to the corresponding 0.5 mL marking on markings 44. This results in pins 36 set into groove 16B, namely segment 17B.

To operate needle syringe 10, which is now set for operation, needle 30 is placed in the liquid/medicine and the liquid is drawn up into cavity 12 by manually pulling up plunger 14. Based on the above described design, owing to pins 36, passing through pin holes 32 and resting in segment 17 of groove, plunger 14 can stably move (without rotation) outwards filling cavity 12, with pins 36 sliding in the selected groove 16. When the correct dose is filled into cavity 12, pins 32 will pass over ledge/stop 19 in groove 16 passing pins 32 into deeper grooves/cutout 21 but still allowing plunger 14 to continue to draw in excess liquid. However, the user will feel pins 36 passing over ledge 19 indicating the dose is reached so they can just extend plunger 14 a little further to grad a few excess mL of liquid.

At this point, needle 30 can be removed from the medicine/liquid and the user can depress plunger 14, pointing syringe 10 upwards, this time ejecting excess medicine/liquid and any air. As noted above, pins 36 are passed ledge 19 into deep groove/cutout 21 so as the user presses out the excess air and liquid by depressing plunger 14 in cavity 12, pins 36 move through deep grooves 21 until the ledge 19 is encountered at which point pins 36 about ledge 19 and prevent plunger from being depressed further without pin 36 retraction. This lets the user know the correct dose is now set.

Moving on to release the dosage, the action of the user pressing down on plunger 14 with the thumb and the fore and middle finger pressing up on the finger rests of finger grip 34, bends out pins 36 over ledge 19, allowing them to pass onto segment 17 of groove 16 thus unlocks plunger 14 allowing the medication to be dispensed at the exact dosage matching the length of segment 17 of groove 16.

Figure 2A:
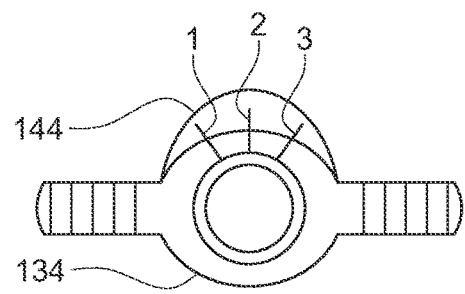
FIG. 2A illustrates an oral syringe cavity from the top with finger clip and indicator markings in accordance with one embodiment.
Figure 2B:
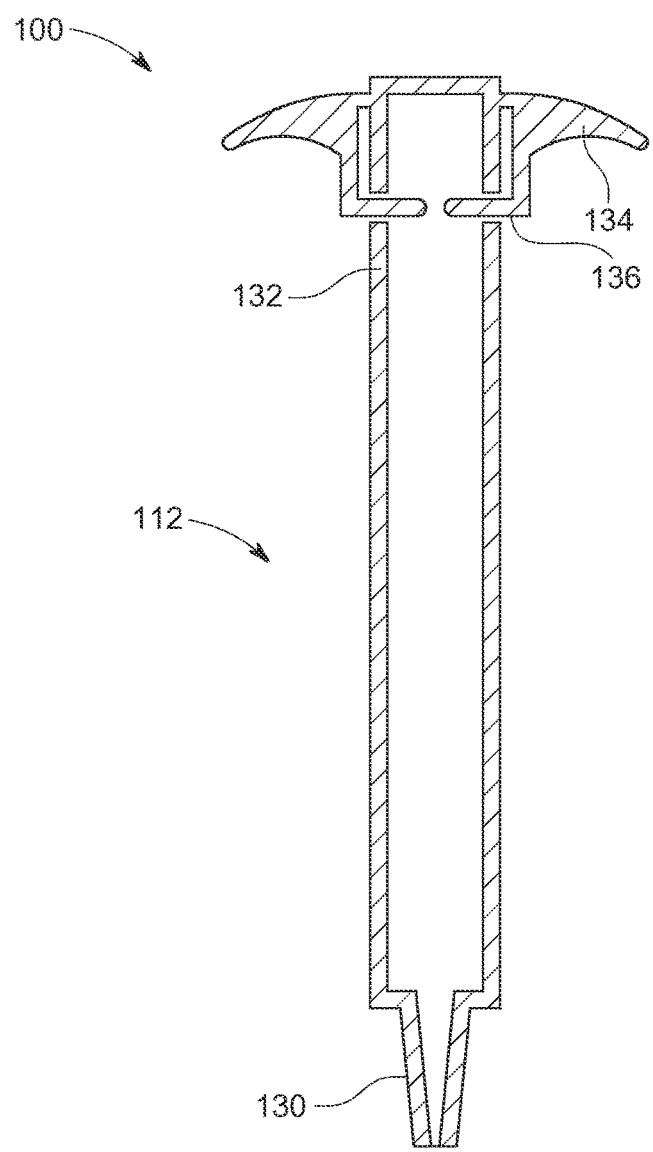
FIG. 2B, illustrates a side view of the cavity in accordance with one embodiment.
Figure 2C:
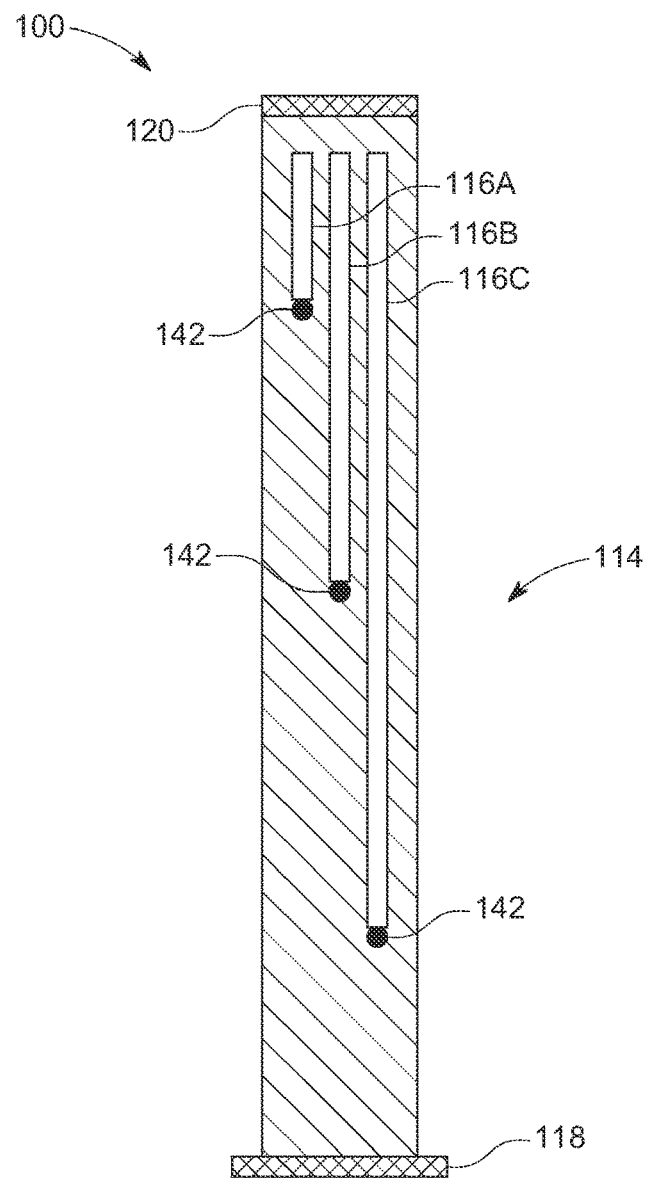
FIG. 2C, illustrates a side view of a plunger for the cavity of the oral syringe in accordance with one embodiment.
Figure 2D:
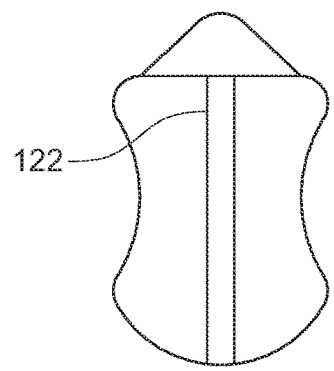
FIG. 2D, illustrates a top view of the plunger with an indicating arrow in accordance with one embodiment.

In another embodiment of the invention as shown in FIGS. 2A-2D, an oral syringe 100 is shown having a cavity 112 and plunger 114. As shown in FIG. 2C, plunger 112 has three grooves 116A-116C, each representing a different dosage. It is understood that plunger 114 could have additional or fewer grooves 116 but for the present example three (3) grooves 116A-116C is used to illustrate the salient features of the invention. At the bottom of plunger 114 is a gasket 118 to slidingly seal against the walls of cavity 112 as in a normal syringe. At the top of plunger 114 is a pressing surface 120. As shown in FIG. 2D, pressing surface 120 has an indicator arrow 122 that is used to correctly orient plunger 114 within cavity 112 in a manner to dispense the correct dose as explained in more detail below.

As shown in FIG. 2B, cavity 112 has an oral nozzle 130, to pin openings 132 as well as a connected finger grip 134 and locking pins 136. Finger grip 134 is fixedly connected to the top of cavity 112. As illustrated in FIG. 2B locking pins 136 extend below grip 134, down the side of cavity 112 into pin openings 132.

As shown in FIG. 2C, plunger 114 has three sets of grooves 116A-116C, each extending a different length along the long axis of plunger 114 and each terminating in a pin lock hole 142. Pins 136 passing through pin opening 132 are configured to rest in one of grooves 116A-116C (not shown but indentations 116A-116C are each a pair of indentations on opposite sides of plunger 114, one for each pin 136). As shown in FIG. 2A the top of finger grip 134 has three indicator markings 144 each of which designate a corresponding one of indentations 116A-116C. By matching indicator arrow 122 of pressing surface 120 of plunger 114 within cavity 112 to one of markings 144, it orients plunger 114 so that pins 136 are in the desired indentation 116.

For example, syringe 100 may be configured to dispense either 0.25 mL, 0.5 mL, or 0.75 mL. As such plunger 14 has three indentations 116A, 116B, and 116C each relating to either 0.25 mL, 0.5 mL, or 0.75 mL respectively. Indicator markings 144 on finger grip 134 likewise would indicate 0.25 mL, 0.5 mL, or 0.75 mL. So, when a user wants to implement syringe 100 for 0.5 mL, the user would rotate plunger 114 until indicator arrow 122 on the top points to the corresponding 0.5 mL marking on markings 144. This results in pins 136 set into indentation 116B.

To operate syringe 100, which is now set for operation, the liquid is drawn up into cavity 112 either by squeezing a connected supply bottle, if it is flexible, or by manually pulling up plunger 114 if the supply bottle is not flexible.

Based on the above described design, owing to pins 136, passing through pin holes 132 and resting in grooves 116, plunger 114 will move outwards filling cavity, with pins 136 sliding in groove 16. When the correct dose is filled into cavity 112, plunger 114 stops and locks at the correct, indicated dosage because pins 36 reach pin locking holes 142. Moving on to release the dosage, the action of the user pressing down on plunger 114 with the thumb and the fore and middle finger pressing up on the fingerrests of finger grip 134, unlocks plunger 114 allowing the medication to be dispensed. The pulling force of finger grip 134 flexes its lower extension allowing pins 136 to release from pin locking holes 142.

In one embodiment, not shown, a supply bottle may be attached to oral nozzle 130 to attach syringe 100 to the supply bottle. If a squeeze bottle is utilized, this results in filling cavity 112 via positive pressure, pushing out plunger 114 while the squeeze bottle is attached to nozzle 130. One possible method of doing this is to have a "key" type arrangement for example with two small pins that protrude out from the base of syringe 100 that fits into a bottle that has two slots that line up with the two pins. You simply line up the syringe so that the two pins align with the two slots, push syringe 100 onto the bottle and rotate. This could make an air-tight fit so that there is no leakage. If a rigid bottle is utilized, this would result in filling syringe 100 via negative pressure and the bottle would be attached to the syringe via friction without a locking mechanism.

While only certain features of the invention have been illustrated and described herein, many modifications, substitutions, changes or equivalents will now occur to those skilled in the art. It is therefore, to be understood that this application is intended to cover all such modifications and changes that fall within the true spirit of the invention.

What is claimed is:

1. A needle syringe comprising:
    a cavity;
    a plunger; and
    a needle for filling and dispensing liquid from said cavity,
        wherein said cavity has a finger clip, the finger clip having movable locking pins,
        wherein said plunger has at least one set of grooves corresponding to a specific dosage for said needle syringe, said specific dosage of said groove being demarked by a marking ledge that indicates a change to a deeper depth section of said groove,
        wherein said locking pins are configured to rest in said at least one set of grooves,
        such that when said plunger is removed, said locking pins pass within a first shallow section of said groove, pass over said ledge, and continue to pass in said deeper depth section of said groove, and
        such that when said plunger is depressed in a first partial dispensing movement, said locking pins pass in said deeper depth section of said groove until said plunger depression is temporarily locked when said locking pins reach said ledge, where the dose remaining in said cavity is said specific dosage, and
        such that when said plunger is depressed in a second full dispensing movement, to dispense said specific dosage, said finger clip is configured to be pulled, deforming a bottom of said finger clip and moving said locking pins over said ledge, allowing said locking pins to re-enter shallow section of said groove and dispensing said specific dosage from said needle syringe.

2. The needle syringe as claimed in claim 1, wherein said plunger has a plurality of sets of grooves each having said shallow sections, said ledges, and said deeper sections, and each of said plurality of sets of grooves corresponding to a different specific dosage.

3. The needle syringe as claimed in claim 2, wherein each of said plurality of grooves each have a different longitudinal location for said ledges along a long axis of said plunger dividing said shallow sections of said grooves, and said deeper sections of said grooves, each of said plurality of grooves corresponding to said different specific dosage.

4. The needle syringe as claimed in claim 2, wherein said plunger has an indicator arrow on the top, and said finger grip has indicator markings, such that said indicator markings on said finger grip correspond to said plurality of grooves having said different specific dosages.

5. An oral syringe comprising:
    a cavity;
    a plunger; and
    a nozzle for filling and dispensing liquid from said cavity,
        wherein said cavity has a finger clip, the finger clip having movable locking pins,
        wherein said plunger has at least one set of grooves corresponding to a specific dosage for said oral syringe, said specific dosage of said groove being demarked by a stop while in said groove,
        wherein said locking pins are configured to rest in said at least one set of grooves,
        such that when said plunger is removed, said locking pins pass within said groove and into said locking hole, filling said cavity with said specific dosage, and
        such that when said plunger is depressed, to dispense said specific dosage, said finger clip is configured to be pulled, deforming a bottom of said finger clip and moving said locking pins out of said locking holes, allowing said locking pins to re-enter said groove and dispensing said specific dosage from said oral syringe.

6. The oral syringe as claimed in claim 5, wherein said plunger has a plurality of sets of grooves each having said grooves and locking holes, and each of said plurality of sets of grooves corresponding to a different specific dosage.

7. The oral syringe as claimed in claim 6, wherein each of said plurality of grooves each have a different longitudinal location along a long axis of said plunger for said stop holes terminating said grooves, each of said plurality of grooves corresponding to said different specific dosage.

8. The oral syringe as claimed in claim 6, wherein said plunger has an indicator arrow on the top, and said finger grip has indicator markings, such that said indicator markings on said finger grip correspond to said plurality of grooves having said different specific dosages.

* * * * *